United States Patent [19]

Rubin et al.

[11] Patent Number: 4,895,874

[45] Date of Patent: Jan. 23, 1990

[54] TUMOR TREATMENT PROCESS AND COMPOSITION

[75] Inventors: David Rubin, 3 Rav Zair; Ely J. Rubin, c/o Israel Medical Research Foundation, P.O. Box 3592, both of Jerusalem, Israel

[73] Assignees: David Rubin; Ely J. Rubin, both of San Diego, Calif.; Adolf W. Schwimmer, Savyon, Israel; Irwin S. Schwartz, Toronto, Canada; Century Laboratories, Inc., Port Washington, N.Y.

[21] Appl. No.: 583,798

[22] Filed: Mar. 1, 1984

Related U.S. Application Data

[63] Continuation of Ser. No. 320,087, Nov. 10, 1981, abandoned.

[51] Int. Cl.$^4$ ............................................. A61K 31/20
[52] U.S. Cl. .................................................... 514/558
[58] Field of Search ........................................ 514/558

[56] References Cited

PUBLICATIONS

Adams, K. R. et al. "Long Chain βω-Dicarboxylic Acids from Spores of Equisetum spp." *J. Chem. Soc.*, 1969 (5), 456–7.

Boyland, E. "142. Experiments on the Chemotherapy of Cancer: 4. Further Experiments with Aldehydes and their Derivatives", Biochem J., 34:1196–1201 (1940).

F. C. Turner, "Experimental Chemotherapy of Tumors in Mice", Journal of the Nat. Cancer Inst., 4:265–270, (1943).

D. L. Woodhouse, "Chemotherapy Investigations in Cancer . . . ", Cancer Research 7:398–401 (1947).

Carter et al., Chemotherapy of Cancer, 2nd ed., John Wiley & Sons, N.Y., N.Y., 1981, pp. 361–365.

Dyer, An Index of Tumor Chemotherapy, Mar. 1949, pp. 10, 11 and 73, NIH (WO 2043).

Carter et al., Chemotherapy of Cancer, John Wiley & Sons, N.Y., N.Y., 1981, pp. 26–43.

Nazzaro–Porro, M. et al., "Identification of Tyrosinase Inhibitors in Cultures of Pityrosporum", *the Journal of Investigative Dermatology*, 71:205–208 (1978).

Breathnach, A. S., et al., "Effect of Dicarboxylic Acids on Normal Human Melanocytes in Dispersed Tissue Culture", *British Journal of Dermatology*, 101, 641–649 (1979).

Nazzaro–Porro, M. et al., "Identification of Tyrosinase Inhibitors in Cultures of Pityrosporum and their Melanocytotoxic Effect", *Pigment Cell*, vol. 4, pp. 234–243 (Karger, Basel 1979).

Nazzaro–Porro, M. et al., "Effect of Azelaic Acid on Human Malignant Melanoma", *The Lancet*, May 24, 1980, pp. 1109–1111.

Morgan, P., "Dicarboxylic Acids", *Kirk–Othmer Encyclopedia of Chemical Technology*, vol. 7, 3rd edition, pp. 614–628 1979, John Wiley & Sons.

Chemical Abstract 94–177606.

Adams, et al., Chemical Abstracts, 71:30012p, 1969.

Ruzicka et al., Chemical Abstracts, 22:2928$^7$, 1928.

Ruzicka et al., Chemical Abstracts 23:111$^7$, 1929.

*Primary Examiner*—Jerome D. Goldberg
*Attorney, Agent, or Firm*—Browdy and Neimark

[57] ABSTRACT

Saturated aliphatic straight chain dicarboxylic acids having a total number of carbon atoms which are divisible by four, are selectively toxic to certain tumor cells while non-toxic to normal cells of the same origin. Octacosanedioic acid is particularly preferred as it is a component of normal blood serum. Compositions containing these compounds may be used in the treatment of certain malignancies.

19 Claims, No Drawings

TUMOR TREATMENT PROCESS AND COMPOSITION

This application is a continuation, of application Ser. No. 320,087, filed Nov. 10, 1981 now abandoned.

FIELD OF THE INVENTION

The present invention relates to the discovery that a certain component of normal blood serum is selectively toxic to certain tumor cells and is not present in the sera of patients afflicted with such tumors, and, more particularly, the present invention relates to pharmaceutical compositions including such compounds and the method of treating tumors against which such compounds are effective, with such compounds.

BACKGROUND OF THE INVENTION

It has been hypothesized that there might be a component of normal individual blood serum which prevents the invasion of certain cancer cells in a healthy individual. Reference to comparative studies of components of normal healthy individual blood sera as compared with cancer patient sera, particularly with respect to organic solvent extracts, could not be found in the literature.

In order to test this hypothesis, a large number of samples of blood from normal individuals and from individuals suffering from various malignancies were taken and the sera were extracted with the following organic solvents:
methylene chloride
benzene
petroleum ether
toluene
diethyl ether.

The sera of both normal individuals and cancer patients were acidified, shaken with the above solvents, separated and evaporated to dryness. In those cases where any discernible residues were found, the only time that there was a difference between the results of the tests with normal individual sera as opposed to cancer patient sera, was found with the diethyl ether extraction. There was a white precipitate in the diethyl ether extracts of all normal individual's sera, although to different extents, but no precipitate from the diethyl ether extracts of cancer patients' sera.

This extract was tested and was found to be extremely toxic to cancer cells while totally non-toxic to normal cells.

SUMMARY OF THE INVENTION

Accordingly, it is an object of the present invention to provide a novel composition which is selectively toxic to certain cancer cells.

It is another object of the present invention to provide a method for the treatment of malignancies against which the compounds of the present invention are active by administration of such compounds.

An analysis of the extract left after diethyl ether extraction of normal patient serum showed this material to be octacosanedioic acid. This compound is a saturated fatty dicarboxylic acid having the formula of HOOC-$(CH_2)_{26}$-COOH.

The cancer patients' sera tested were from individuals having the following malignancies:
1. breast carcinoma
2. carcinoma of the colon
3. bronchogenic carcinoma.

DETAILED DESCRIPTION OF PREFERRED EMBODIMENTS

In order to test for anti-cancer activity of this compound, the disodium salt of octacosanedioic acid was synthesized and then introduced in different concentrations to cancer cell suspensions of the above mentioned neoplasms in saline solutions, as well as to suspensions of normal cells of the same origin. This treatment resulted in lysis of the cancer cells starting within 20 minutes at a concentration of 0.0001%. No damage occurred to the normal cells except for the slight damage that occurred to these cells while making the suspension, which damage was equal in both groups of the cells.

In order to determine whether this property was unique to this particular dicarboxylic acid, similar tests were conducted with homologs of this material which are available commercially. The results are indicated in Table 1.

TABLE 1

| Formula | Common Name | Effect |
|---|---|---|
| 1. HOOC—$CH_2$—COOH | malonic | no lytic effect |
| 2. HOOC—$(CH_2)_2$—COOH | succinic | slight lytic effect at concentration of 0.1% |
| 3. HOOC—$(CH_2)_3$—COOH | glutaric | no lytic effect |
| 4. HOOC—$(CH_2)_4$—COOH | adipic | no lytic effect |
| 5. HOOC—$(CH_2)_5$—COOH | pimelic | no lytic effect |
| 6. HOOC—$(CH_2)_6$—COOH | suberic | a lytic effect at concentration of 0.001% |
| 7. HOOC—$(CH_2)_7$—COOH | azelaic | no lytic effect |
| 8. HOOC—$(CH_2)_8$—COOH | sebacic | no lytic effect |
| 9. HOOC—$(CH_2)_9$—COOH | | no lytic effect |
| 10. HOOC—$(CH_2)_{10}$—COOH | | a lytic effect at at concentration of 0.005% |
| 11. HOOC$(CH_2)_{14}$—COOH | thapsic | a lytic effect at concentration of 0.0005% |

Acids 1–10 of the above table were obtained from Sigma Chemical Company and acid No. 11 (thapsic acid) was obtained from Aldrich Chemical Company.

In all of the tests listed in Table 1, the disodium salt of the dicarboxylic acid was used in order to increase the solubility. The concentrations that were used were far lower than those necessary to affect the osmolarity. Thus, no lysis could be contributed to osmotic pressure. For each of the tests in Table 1 it was further noted that normal cells of the same origin were not affected.

A study of this table shows that lysis of cancer cells occurs when the number of —$C_2H_4$— groups in the compound is odd. In other words, when the total carbon atom count of the compounds is divisible by 4, the desired effect is observed. Furthermore, it is evidenced that the longer the chain, the stronger the lytic effect.

The present invention comprehends the use of any straight-chain saturated aliphatic dicarboxylic acid or pharmaceutically acceptable salt thereof whose total number of carbon atoms is divisible by 4 for the treatment of various malignancies against which such compounds are effective in vitro. More particularly, such dicarboxylic acids having a total number of 8, 12, 16, 20, 24 or 28 carbon atoms are preferred compounds for use in the present invention.

While the tests discussed hereinabove relate only to breast carcinoma, carcinoma of the colon, and bronchogenic carcinoma, it will be readily apparent to those skilled in the art that by routine experimentation it can be determined whether the compounds of the present invention would also be effective against any other given neoplasm. This test would simply involve the preparation of a suspension of the cancer cells of the neoplasm in question in saline solution, and treatment in vitro with one of the compounds of the present invention to determine whether lysis of the cancer cells results. If no lysis results, then it is clear that the compounds of the present invention are ineffective against this particular type of neoplasm. If lysis results, then it would be expected that the compounds of the present invention would indeed be effective against these tumors in vivo.

Succinic acid has been reported to have a low order of toxicity in animals and has been used as an acidulant in foods. Subaric acid also has low toxicity. The higher dibasic acids ($C_8$ and higher) are reported to have lower internal toxicity. As pointed out hereinabove, octacosanedioic acid is a component of normal human blood serum.

The compounds in accordance with the present invention are preferably administered in the form of their sodium salt in order to increase their solubility, although other pharmaceutically acceptable salts may also be used for this purpose. They are preferably administered orally and they may be in the form of a composition with the usual pharmaceutically acceptable carriers and/or excipients. The precise dosage must be determined empirically and will differ depending upon the condition of the patient. Relatively small amounts of the compound of the present invention can be administered at first with steadily increasing daily dosages if no adverse effects are noted. A dosage of 15 g/day, for example, may be found to be preferred. Of course, the maximum safe toxicity dosage as determined in routine animal toxicity tests should never be exceeded. Furthermore, the dosage should be monitored to avoid any side effects due to the release of toxins caused by the dying cancer cells.

Anti-ammonia intoxication treatment, such as that used for treatment of cirrhosis of the liver, should be used to avoid such side effects.

Besides oral administration, the dicarboxylic acids in accordance with the present invention may be administered by any means of parenteral administration.

The theory behind the effectiveness of the compounds of the present invention is not fully understood. It is known, however, that many dicarboxylic acids are inhibitors of tyrosinase and that tyrosinase activity is caused by many malignant tumors. In view of the possibility that the action of these compounds on tyrosinase has something to do with their effectiveness, it may also be worthwhile to administer concurrently other inhibitors of tyrosinase, such as chemicals that can chelate or complex copper ions. Such inhibitors include D-penicillamine, p-aminobenzylic acid, BAL (dimercaprol), thioproline, etc.

Octacosanedioic acid may be prepared in accordance with classical methods of production of higher dicarboxylic acids. It is not believed that this compound has ever been prepared in pure form prior to the present invention, although those of ordinary skill in the art would find no difficulty in arriving at methods for the preparation of this compound, once the desirability of making it was known.

It will be obvious to those skilled in the art that various changes may be made without departing from the scope of the invention and the invention is not to be considered limited to what is described in the specification.

What is claimed is:

1. A method for the treatment of a carcinoma neoplasm comprising administering to a patient having such a carcinoma neoplasm, an amount effective to cause the death of at least some of the cells of said neoplasm of a saturated straight chain aliphatic dicarboxylic acid, or a pharmaceutically acceptable salt thereof, having a total number of carbon atoms which is divisible by four, said total number of carbon atoms being a number such that said dicarboxylic acid or salt is effective and at least 12, wherein said carcinoma neoplasm is one against which said dicarboxylic acid is toxic when a cell suspension thereof is treated with said compound in vitro.

2. A method in accordance with claim 1, wherein the total number of carbon atoms divisible by four is between 12 and 28, inclusive.

3. A method in accordance with claim 1, wherein said dicarboxylic acid is octacosanedioic acid or a pharmaceutically acceptable salt thereof.

4. A method in accordance with claim 1, wherein said carcinoma neoplasm is breast carcinoma, carcinoma of the colon or bronchogenic carcinoma.

5. A method for the treatment of a neoplasm comprising administering to a patient having such a neoplasm, an amount effective to cause the death of at least some of the cells of said neoplasm of a saturated straight chain aliphatic dicarboxylic acid, or a pharmaceutically acceptable salt thereof, having a total of 16, 20, 24 or 28 carbon atoms, wherein said neoplasm is one against which said dicarboxylic acid is toxic when a cell suspension thereof is treated with said compound in vitro.

6. A method in accordance with claim 5, wherein said dicarboxylic acid is octacosanedioic acid or a pharmaceutically acceptable salt thereof.

7. A method for causing the death of neoplastic cells comprising causing said cells to be contacted by an amount effective to cause the death of at least some of said cells, of a saturated straight chain aliphatic dicarboxylic acid, or a pharmaceutically acceptable salt thereof, having a total number of carbon atoms which is divisble by four, said total number of carbon atoms being a number such that said dicarboxylic acid or salt is effective and at least 12, wherein said neoplastic cells are cells which are sensitive to treatment with the dicarboxylic acid or salt being used.

8. A method in accordance with claim 7, wherein said neoplastic cells are cells of a carcinoma neoplasm.

9. A method in accordance with claim 8, wherein said carcinoma neoplasm is a breast carcinoma, carcinoma of colon or bronchogenic carcinoma.

10. A method in accordance with claim 7, wherein the total number of carbon atoms divisible by four is between 12 and 28, inclusive.

11. A method in accordance with claim 8, wherein the total number of carbon atoms divisible by four is between 12 and 28, inclusive.

12. A method in accordance with claim 9, wherein the total number of carbon atoms divisible by four is between 12 and 28, inclusive.

13. A method in accordance with claim 7, wherein said dicarboxylic acid is octacosanedioic acid or a pharmaceutically acceptable salt thereof.

14. A method in accordance with claim 8, wherein said dicarboxylic acid is octacosanedioic acid or a pharmaceutically acceptable salt thereof.

15. A method in accordance with claim 9, wherein said dicarboxylic acid is octacosanedioic acid or a pharmaceutically acceptable salt thereof.

16. A composition for the treatment of malignancies sensitive to treatment with the dicarboxylic acid or salt of the composition, comprising an amount effective to cause the death of at least some of the cells of said malignancy of a straight chain aliphatic saturated dicarboxylic acid, or a pharmaceutically acceptable salt thereof, having a total of 16, 20, 24 or 28 carbon atoms, and a pharmaceutically acceptable carrier.

17. The composition in accordance with claim 16, wherein said dicarboxylic acid is octacosanedioic acid or a pharmaceutically acceptable salt thereof.

18. The composition in accordance with claim 17, wherein said octacosanedioic acid is in the form of the disodium salt thereof.

19. The composition in accordance with claim 16, wherein said dicarboxylic acid is in the form of the disodium salt thereof.

* * * * *